United States Patent [19]

Hartwell

[11] Patent Number: 4,499,591

[45] Date of Patent: Feb. 12, 1985

[54] FLUOROSCOPIC FILTERING

[76] Inventor: Gary Hartwell, Rte. 1, Box 260X, Troy, Va. 22974

[21] Appl. No.: 442,318

[22] Filed: Nov. 17, 1982

[51] Int. Cl.$^3$ .............................................. A61B 6/00

[52] U.S. Cl. .................................... 378/062; 378/156

[58] Field of Search ..................... 378/157, 158, 16, 5, 378/156, 99, 62

[56] References Cited

U.S. PATENT DOCUMENTS

| | | | |
|---|---|---|---|
| 1,624,443 | 4/1927 | St. John . | |
| 2,225,940 | 12/1940 | Grossman . | |
| 2,901,631 | 8/1959 | Hansen et al. . | |
| 3,402,292 | 9/1968 | Baecklund . | |
| 3,515,874 | 6/1970 | Bens et al. | 378/156 |
| 3,854,049 | 12/1974 | Mistretta et al. | 378/157 |
| 3,860,817 | 1/1975 | Carmean | 378/156 |
| 3,976,889 | 8/1976 | Noske et al. . | |
| 4,029,963 | 6/1977 | Alvarez et al. | 378/157 |
| 4,101,766 | 7/1978 | Minami . | |

FOREIGN PATENT DOCUMENTS

| | | |
|---|---|---|
| 1178954 | 10/1964 | Fed. Rep. of Germany . |
| 2212105 | 9/1973 | Fed. Rep. of Germany . |

OTHER PUBLICATIONS

Kuhn, H., "Reducing the Patient Dose by Prefiltration," *Electromedica,* Feb. 1982, pp. 41–43.

Rossi, R. P., "Reduction of Radiation Exposure in Radiography of the Chest," *Radiology,* 144, Sep. 1982, pp. 904–914.

Doi, K., et al., "Development of a Rigid Fluorescent X-ray Source for Monoenergetic Radiation Studies in Radiographic Imaging," *Radiology,* 142: 233–236, Jan. 1982.

*Primary Examiner*—Alfred E. Smith
*Assistant Examiner*—T. N. Grigsby
*Attorney, Agent, or Firm*—Stanley J. Price, Jr.; John M. Adams

[57] ABSTRACT

A radiation source emits a beam of penetrating radiation toward an examination object. A protective filter, fabricated of yttrium foil attached to a bakelite card, is positioned in the path of the radiation beam between the source and the examination object. The yttrium filter has a preselected critical absorption edge operable to obstruct from the beam photon energy below 20 keV and permit a filtered beam having a photon energy above 20 keV to pass through the examination object. The filtered radiation emerging from the examination object is detected by preselected means, such as illuminated film, an X-ray intensifier, a CT scanner, or the like. The detector generates an output signal corresponding to the intensity of the emerging filtered radiation. An image processor converts the output signals to a radiographic image displaying the examination object.

12 Claims, 3 Drawing Figures

FLUOROSCOPIC FILTERING

BACKGROUND OF THE INVENTION

1. Field of the Invention

This invention relates to fluoroscopic imaging and more particularly to apparatus for limiting the radiation dosage to an examination object within a limited photon energy range.

2. Description of the Prior Art

It is well known in the art of fluoroscopy, in both medical and industrial applications, to limit or reduce the level of radiation exposure to the examination object by the use of filters. As disclosed in U.S. Pat. No. 3,860,817, during fluoroscopy, the X-ray beam, emitting from a source, is filtered so that substantially only radiation, within a preselected spectral band or window, impinges on the patient or the examination object. Thus, a minimumm of the radiation energy is wasted in a film changer intensifying screen so that the ratio of information output to patient dose is optimized. Preferably, the material for the filter is chosen on the basis of a preselected photon energy band or window, which will pass through the filter and be absorbed by the examination object.

U.S. Pat. No. 2,225,940 discloses a movable wedge-shaped filter made of aluminum. The filter is positioned transversely to the radiation beam, and movement of the filter transversely to the beam presents different thicknesses of the filter to be traversed by the beam. One undesirable feature of the graduated or wedge filters is the hardening of the beam which occurs and the resulting image has a quality degraded to a degree that is unacceptable.

The use of the known graduated filters for filtering the upper critical absorption edge (K-edge energy) spectral range of the X-ray photon energy requires an increase in the X-ray tube current to increase the intensity of the X-ray photon energy emitted from the tube. This has the undesirable consequence of exposing the patient or the examination object to undesirably high radiation dosage during fluoroscopy. Also, increasing the X-ray tube current results in excessive X-ray tube loading. Other examples of fluoroscopy filtration are disclosed in U.S. Pat. Nos. 1,624,443; 2,901,631; 3,402,292; 3,976,889; 4,101,766 and 4,246,488.

Overall, the known fluoroscopy filtration devices have been directed to isolating spectral distributions that exploit absorption characteristics of tissue and contrast media for improved images. However, these efforts have not been effective to optimize the filter material for routine fluoroscopy and, in particular, in the fluoroscopy of soft tissue and bones. Therefore, there is need in fluoroscopy filtration to provide a filter operable in the fluoroscopy of both soft tissue and bones and composed of a material having a critical absorption edge (K-edge energy) that eliminates the photon energy levels of the radiation beam that play little or no role in the imaging process.

SUMMARY OF THE INVENTION

In accordance with the present invention, there is provided apparatus for limiting the radiation dosage to an examination object within a limited photon energy range that includes a source of radiation for emitting a beam of penetrating radiation toward the examination object. A protective filter is positioned in the path of the beam between the source and the examination object. The protective filter is composed of a material having a preselected absorption edge energy operable to obstruct from the beam photon energy below 20 keV and permit a filtered beam having photon energy above 20 keV to pass through the examination object. A radiation detector is positioned to receive the filtered radiation emerging from the examination object. The radiation detector is operable to generate an output signal corresponding to the intensity of the emerging filtered radiation. Image processing means converts the output signal to a radiographic image displaying the examination object.

Preferably, the filter is fabricated of a material capable of eliminating photon energy levels below the 20 keV range, thereby eliminating photon energy levels that do not contribute to the spectral quality of the radiographic image of the examination object. Preferably, the filter is a metallic material having a preselected thickness in the range of 100 microns to 250 microns. Thus, the filter is relatively thin and transparent to higher photon energy levels which contribute to the spectral quality of the radiographic image.

Accordingly, the principal object of the present invention is to provide a fluoroscopic filter composed of a preselected material operable to filter photon energy below 20 keV from a radiation beam directed to an examination object.

Another object of the present invention is to provide for routine radiography a filter operable to remove from the radiation beam photon energy below 20 keV without reducing the image quality.

Another object of the present invention is to provide a reduction in radiation dosage directed upon an examination object by the use of a rare earth metal filter that removes or blocks the photon energy of a radiation beam below a preselected limit, which contributes little to the imaging process, and permitting photon energy above a preselected keV level to penetrate the examination object.

An additional object of the present invention is to provide a fluoroscopic filter that blocks photon energy from a radiation beam below 20 keV eliminating nonuseful photon energy and thereby utilizing the higher photon energy of a radiation beam.

These and other objects of the present invention will be more completely disclosed and described in the following specification, the accompanying drawings, and the appended claims.

DESCRIPTION OF THE PREFERRED EMBODIMENTS

Figure 1:
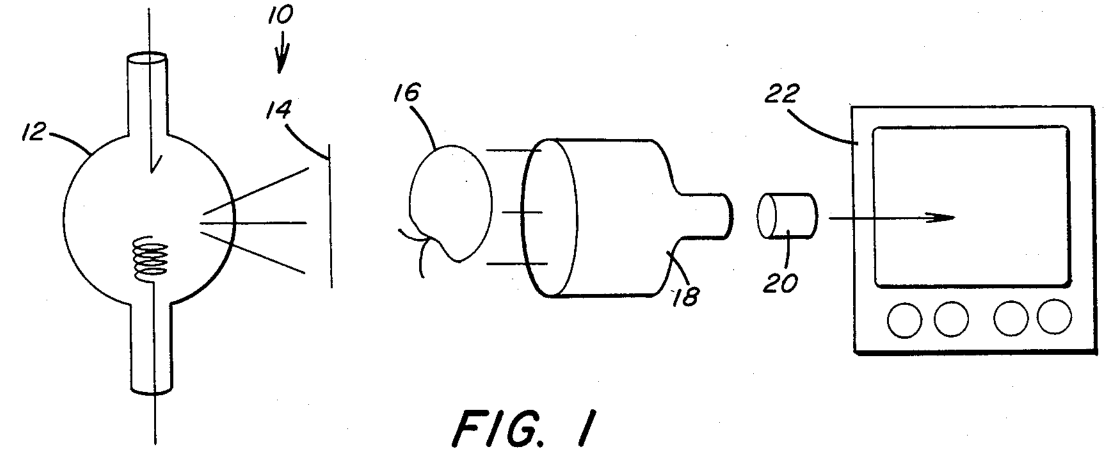
FIG. 1 is a schematic representation of a fluoroscopic imaging system, illustrating a filter positioned between a radiation source and an examination object in accordance with the present invention.

Referring to the drawings, and particularly to FIG. 1, there is illustrated a fluoroscopic imaging system generally designated by the numeral 10 for use in examination of the condition of an internal structure of an object, for example, a patient in medical diagnosis or an object to be examined in an industrial application. Radiation from a source, such as a radiation generator, having a minimum potential of 150 kvp and a maximum current capacity of 1,300 ma is emitted from an X-ray tube 12. A suitable X-ray tube is one having a high flux X-ray source and a heat capacity of a selected range. A filter 14, preferably fabricated of metallic foil attached to a bakelite card, is positioned opposite the slot in the generator 12 through which the radiation beam passes. The filter 14 is centered in the path of the radiation beam between the radiation source and an object 16 to be examined, such as soft tissue or bone structure of a patient. The filter 14 is operable to obstruct a preselected energy photon level of the radiation beam, and most particularly to obstruct the photon radiation level of the beam which is known not to contribute to the quality of the radiographic image to be produced. Most preferably, the filter 14 is composed of a material having a critical absorption edge (K-edge energy) that blocks the passage of radiation beam photon energy below 20 keV and permit higher levels of photon energy of the radiation beam to pass through the filter and through the examination object 16.

The filtered radiation beam is directed to an image intensifier 18. The output of the image intensifier 18 is converted to an output signal in the form of light. The light images are then converted by a vidicon camera 20 to electronic output signals representing the radiographic image. The electronic output from the vidicon camera 20 is converted by a video monitor 22 to a video display on a screen.

Figure 2:
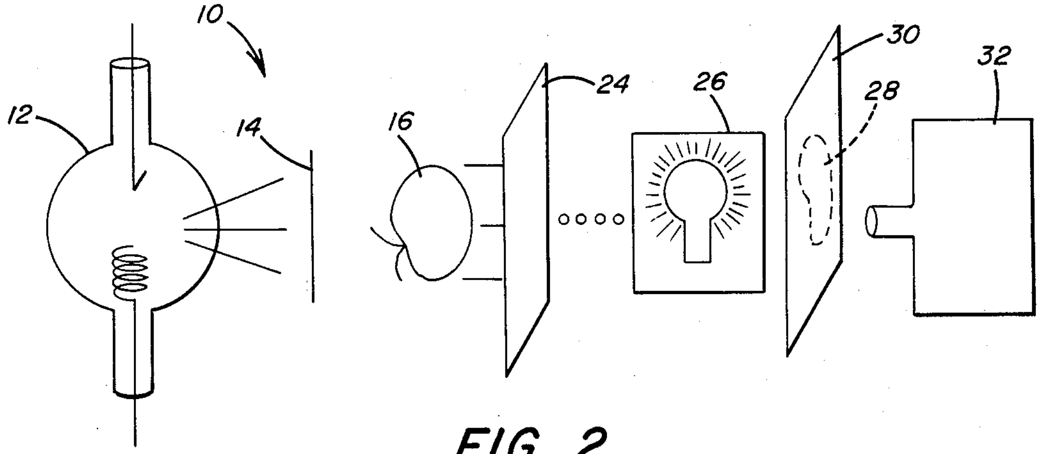
FIG. 2 is a schematic representation, similar to FIG. 1, illustrating another embodiment of an imaging system to be used with the fluoroscopic filter of the present invention.

In an alternate embodiment, as illustrated in FIG. 2, the radiation beam passes through the filter 14, as above described, with the photon energy below 20 keV being blocked, and the higher photon energy of the radiation beam passes through the examination object 16 and is directed upon a suitable detector device, such as on 35 mm. cine or cut film 24. The images on the cut film 24 are transilluminated by an illuminator 26. The illuminator 26 illuminates an image 28 of the examination object 16 on a second film 30. The image 28 is viewed by a high sensivity, low noise vidicon camera 32. Preferably, the camera 32 includes a plumbicon-type video tube. The vidicon camera 32 converts the radiation in the form of the image 28 cast on the film 30 to an output signal proportional in magnitude to the filtered beam of radiation. The output signal from the camera 32, in one mode, is transmitted to a digitizer, which converts the output signal to a digital signal suitable for storage in a computer for later retrieval or, in a second mode, to a digital imaging processor for processing and image enhancement for video display on a suitable viewer as well known in the art.

With the embodiments of the present invention illustrated in FIGS. 1 and 2, the filter 14 is positioned a preselected distance from the beam outlet of the X-ray tube 12. The radiation beam passes through the filter 14 before it penetrates the examination object 16. The filter 14 is independently supported in a suitable frame positioned between the X-ray tube 12 and the examination object 16.

Figure 3:
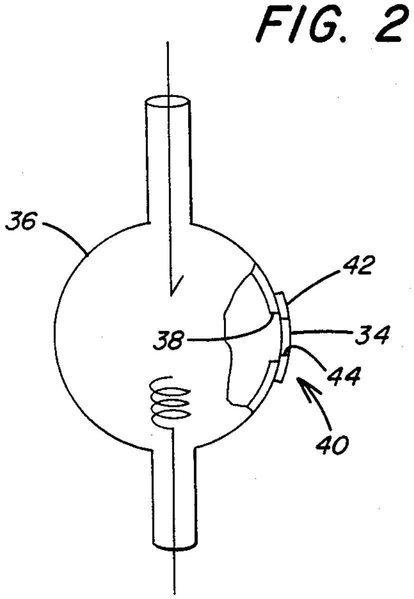
FIG. 3 is a schematic representation of a radiation generator, having a slot through which the radiation beam passes and a filter, in accordance with the present invention, secured to the generator over the slot.

In a further embodiment of the present invention, as shown in FIG. 3, a filter 34 is secured to an X-ray tube 36 of the type described above for the X-ray tube 12. The X-ray tube 36 includes a slot 38 through which a beam of penetrating radiation is emitted toward the examination object. A radiation beam limiting device, generally designated by the numeral 40, is secured to the outer surface of the X-ray tube in overlying relation with the slot 38. The radiation beam limiting device 40 includes a frame 42 having a slot 44 positioned in the center of the radiation beam emitted from the X-ray tube 36. The filter 34 is supported in the frame 42 in overlying relation with the slot 44. The frame 42 is designed to facilitate efficient removal and insertion of the filter 34 into and out of position over the slot 44.

Preferably, the filter 14 used in the embodiments shown in FIGS. 1 and 2, as well as, the filter 34 used in the embodiment shown in FIG. 3 is a metallic foil composed of a preselected rare earth metal. Preferably, the foil forming both the filters 14 and 34 has a thickness in the range between about 100 to 250 microns. Most preferably, the filters 14 and 34 are fabricated of a filter material and having the above thickness range and a critical absorption edge of less than 20 keV. With a filter having these features, the examination object 16 is exposed to a "spectral window" of radiation having a photon energy level of the maximum detection efficiency. The filter of the present invention filters from the radiation beam, photon energy below the energy of the critical absorption edge of the filter material.

By filtering out photon energy below a critical absorption edge of 20 keV, much of the level of the photon energy level of the radiation beam, which does not contribute to the efficiency of the radiographic image, is obstructed by the filter and is not absorbed by the examination object. Therefore, only the higher photon energy levels which contribute to the efficiency of the radiographic image are permitted to pass through the filter and the examination object. By eliminating from the radiation beam photon energy levels below the 20 keV absorption edge coefficient of the respective filters 14 and 34, the examination object exposure to radiation is reduced from between about 40 to 70 percent without encountering a significant loss in the information content of the radiographic image. Thus, the filter of the present invention eliminates from the radiation beam, the photon energy which contributes little or nothing to the quality of the radiographic image of the examination object.

A filter material operable for use in the present invention is one having a filter K-edge energy of 20.0 keV or less. Preferably, the filter material is a rare earth metal selected from the group consisting essentially of yttrium, zirconium, niobium, and molybdenum. These metals have a filter K-edge energy of 20.0 keV or less. With the above described filter apparatus using these rare earth metals as the filter material, the filter is very thin and largely transparent to photons above the energy level of the K-edge energy of the absorption material. By concentrating on the K-edge energy of the filter material, in accordance with the present invention rather than the thickness of the filter material, the photon energy of the radiation beam below 20 keV is eliminated, thus eliminating the portion of the photon energy levels of the radiation beam considered to contribute little to the quality of the radiographic image.

The following examples illustrate the present invention, but are not intended as a limitation thereof.

EXAMPLE 1

A filter was fabricated of 0.127 mm yttrium foil, 50 mm by 50 mm attached to a 0.25 mm bakelite card supported in the frame of the radiation beam limiting device. The card frame was secured, in surrounding relation, to the filter slot of an X-ray tube. The card frame was positioned on the X-ray tube so that the yttrium foil was positioned in the center of the radiation beam emitted by the X-ray tube through the tube slot. The radiation beam limiting device included a fixed filter of 2.5 mm aluminum at a half-value thickness of 80 kVp. The addition of the yttrium foil filter increased the half-value thickness to 5.3 mm of aluminum.

The X-ray exposures were measured in air at a point 1.0 meter from the focal point by a MDH model 1015 dosimeter having a calibrated 6 cc chamber. The dosimeter readings were corrected for energy response and atmospheric pressure. The examination objects included 3M pelvis and knee phantoms. Radiographic images were taken on film with and without the yttrium filter in combination with the fixed filtration with the X-ray tube. Each phantom was exposed to a radiation beam filtered by the yttrium filter to a density approximately equal to that of the standard films. Exposure of the knee measured 89 mR with conventional filtration and 21 mR with the yttrium filter. Exposures of the pelvis measured 126 mR with the conventional filtration and 47 mR with the yttrium filter. Films were taken with and without the yttrium filter of each phantom at varying kiloelectron volts (keV). Ten radiologists evaluated the phantom films taken with and without the yttrium filter and all the radiologists selected the films taken with the yttrium filter as having the best image quality.

EXAMPLE 2

The above-described apparatus of Example 1 was used to evaluate the yttrium filter under clinical conditions in which the extremities of 24 patients were radiographed with and without the yttrium filter associated with the radiation beam limiting device of the X-ray tube. Lateral films of the extremities were taken with the yttrium filter. A corresonding set of films were taken using conventional radiographic filter techniques. The yttrium filter films required a 40 percent greater X-ray tube load than the conventional films; however, this increase in tube loading was below the range of tube loading required with standard graduated filters known to result in higher tube loading and even tube loading which approaches overload conditions.

The 24 yttrium filter films were randomly distributed on an automatic viewer without identification as to whether they were taken with or without the yttrium filter. The films were evaluated by four radiologists on the basis of the quality of the bone and soft tissue detail and overall information. All of the radiologists selected the yttrium filtered films for soft tissue imaging and the conventional filtered films for bone imaging. However, the radiologists found that the overall information content of the images to be substantially equal for both the films taken with the yttrium filter and those taken without the yttrium filter and with only the conventional filtration.

As a result of the above investigations, it was concluded that a filter having a critical absorption edge capable of filtering out from the radiation beam photon energy levels below 20 keV to be applicable as a universal filter. Further, the filter system of the present invention is preferred in cases of frequent repeat examinations or where multiple examinations are utilized, such as prenatal or neonatal radiology and in the emergency room. The use of the above disclosed rare earth metals in combination with other metals is adaptable as a replacement for graduated filters in the examination of the upper dorsal spine.

According to the provisions of the patent statutes, I have explained the principle, preferred construction and mode of operation of my invention and have illustrated and described what I now consider to represent its best embodiments. However, it should be understood that within the scope of the appended claims, the invention may be practiced otherwise than as specifically illustrated and described.

I claim:

1. Apparatus for limiting the radiation dosage to an examination object within a limited photon energy range comprising, a source of radiation including an X-ray generator for emitting a beam of penetrating radiation toward the examination object, said X-ray generator having a slot through which said beam of radiation passes, a radiation beam limiting device positioned on said X-ray generator in overlying relation with said slot, a protective filter positioned in the path of said beam between said source and the examination object, said protective filter being supported by said radiation beam limiting device such that the center of the radiation beam emitted from the X-ray generator passes through said protective filter, said protective filter composed of a material having a preselected critical absorption edge energy operable to obstruct from the beam photon energy below 20 keV and permit a filtered beam having a photon energy above 20 keV to pass through the examination object, a radiation detector positioned to receive the filtered radiation emerging from the examination object, said radiation detector being operable to generate an output signal corresponding to the intensity of the emerging filtered radiation, and image processing means for converting said output signal to a radiographic image displaying the examination object.

2. Apparatus as set forth in claim 1 in which, said protective filter includes a rare earth metallic foil.

3. Apparatus as set forth in claim 2 in which, said rare earth metallic foil is selected from a group of filter materials consisting essentially of yttrium, zirconium, niobium and molybdenum.

4. Apparatus as set forth in claim 2 in which, said foil has a preselected thickness in a range between about 100 microns to 250 microns.

5. Apparatus as set forth in claim 2 which includes, a fixed filter of a preselected filter material positioned in said radiation beam limiting device, and said foil filter being superimposed on said fixed filter such that the center of the radiation beam passes through said fixed filter and said foil filter.

6. Apparatus as set forth in claim 1 in which, said radiation beam limiting device is positioned a preselected distance from said radiation source and between said radiation source and the examination object, and said protective filter is supported by said radiation beam limiting device such that the center of the radiation beam emitted from said radiation source passes through said protective filter.

7. Apparatus for limiting the radiation dosage to an examination object within a limited photon energy comprising, a source of radiation for emitting a beam of penetrating radiation toward the examination object, a radiation beam limiting device positioned a preselected distance from said radiation source and between said radiation source and the examination object, a protective filter positioned in the path of said beam between said radiation source and the examination object, said protective filter being supported by said radiation beam limiting device such that the center of said radiation beam emitted from said radiation source passes through said protective filter, said protective filter including metallic foil having a preselected thickness in the range between about 100 microns to 250 microns and is operable to obstruct from the radiation beam photon energy less than 20 keV and permit photon energy greater than 20 keV to pass through said metallic foil and the examination object, a radiation detector positioned to receive the filtered radiation emerging from the examination object, said radiation detector being operable to generate an output signal corresponding to the intensity of the emerging filtered radiation, and image processing means for converting said output signal to a radiographic image displaying the examination object.

8. Apparatus as set forth in claim 7 in which, said protective filter is a metallic foil selected from the group of rare earth metals consisting essentially of yttrium, zirconium, niobium, and molybdenum.

9. A method for limiting the radiation dosage to an examination object comprising the steps of, emitting a beam of penetrating radiation from a source of radiation toward the examination object, positioning a filter material a preselected distance from the source of radiation and the examination object between the source of radiation and the examination object, providing a filter material having a preselected thickness in the range between about 100 microns and 250 microns and selected from the group of rare earth metals consisting essentially of yttrium, zirconium, niobium, and molybdenum, obstructing radiation beam photon energy of 20 keV and less by the filter material, permitting photon energy of the radiation beam above 20 keV to pass through the examination object, detecting the filtered radiation emerging from the examination object, and processing the emerging filtered radiation to provide a radiographic image of the examination object corresponding to the intensity of the emerging filtered radiation.

10. A method as set forth in claim 9 which includes, filtering from the radiation beam photon energy below 20 keV by the filter material having a critical absorption energy edge which eliminates from the radiation beam that level of photon energy which does not contribute to the quality of the radiographic image.

11. A method for limiting the radiation dosage to an examination object comprising the steps of, emitting a radiation beam from an X-ray generator to the examination object, supporting a filter material on the X-ray generator such that the center of the radiation beam passes through the filter, selecting the filter material having a preselected thickness in the range between about 100 microns and 250 microns and from the group of rare earth metals consisting essentially of yttrium, zirconium, niobium, and molybdenum, obstructing by the filter material radiation beam photon energy of 20 keV and less and being transparent to photon energy above 20 keV, permitting photon energy of the radiation beam above 20 keV to pass through the examination object, detecting the filtered radiation emerging from the examination object, and processing the emerging filtered radiation to provide a radiographic image of the examination object corresponding to the intensity of the emerging filtered radiation.

12. A method as set forth in claim 11 which includes, filtering from the radiation beam photon energy which does not contribute to the quality of the radiographic image.

* * * * *

REEXAMINATION CERTIFICATE (1168th)

United States Patent [19]

[11] B1 4,499,591

Hartwell

[45] Certificate Issued Dec. 12, 1989

[54] FLUOROSCOPIC FILTERING

[75] Inventor: Gary Hartwell, Troy, Va.

[73] Assignee: The University of Virginia Alumni Patents Foundation

Reexamination Request:
No. 90/001,664, Dec. 12, 1988

Reexamination Certificate for:

| | |
|---|---|
| Patent No.: | **4,499,591** |
| Issued: | **Feb. 12, 1985** |
| Appl. No.: | **442,318** |
| Filed: | **Nov. 17, 1982** |

[51] Int. Cl.⁴ .................................... A61B 6/00
[52] U.S. Cl. .................................... 378/62; 378/156

[56] References Cited

PUBLICATIONS

"Nondestructive Testing Handbook," McMaster, The Ronald Press Company, 1963, p. 27-26.
Reduction of Dose by Filtration in Pediatric Fluoroscopy and Fluorography, Heinrich, H. and Schuster, W., Ann. Radiol., 1976, 19(1), pp. 57-66.
Duocon-1, Duocon-2, Duocon-3 X-Ray Collimators, The Machlett Laboratories, Inc., Stamford, Conn. 06907, Mar. 1969.
Collimators General Instructions, The Machlett Laboratories, Inc., Stamford, Conn. 06907, Mar. 1970.
Duocon's Illustrated Parts Price List, The Machlett Laboratories, Inc., Stamford, Connecticuit, 06907, Nov. 1967.

*Primary Examiner*—Craig E. Church

[57] ABSTRACT

A radiation source emits a beam of penetrating radiation toward an examination object. A protective filter, fabricated of yttrium foil attached to a bakelite card, is positioned in the path of the radiation beam between the source and the examination object. The yttrium filter has a preselected critical absorption edge operable to obstruct from the beam photon energy below 20 keV and permit a filtered beam having a photon energy above 20 keV to pass through the examination object. The filtered radiation emerging from the examination object is detected by preselected means, such as illuminated film, an X-ray intensifier, a CT scanner, or the like. The detector generates an output signal corresponding to the intensity of the emerging filtered radiation. An image processor converts the output signals to a radiographic image displaying the examination object.

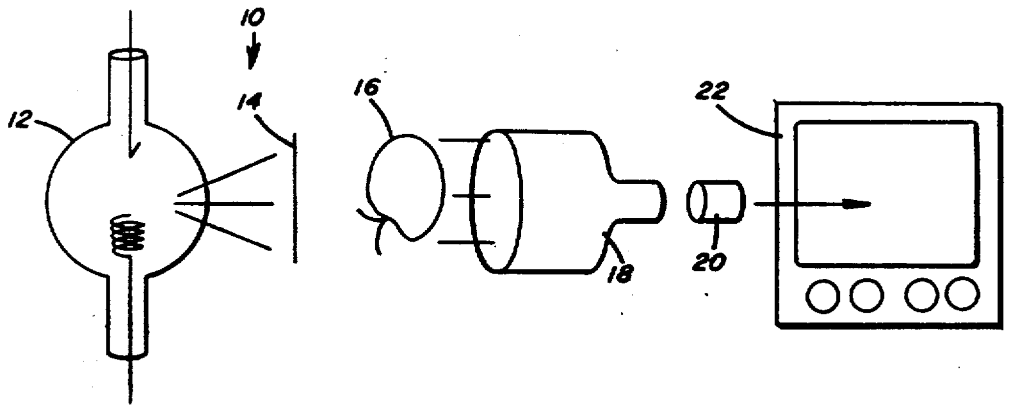

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 45–61:

A filter material operable for use in the present invention is one having a filter K-edge energy of [20.0] *20* keV or less. Preferably, the filter material is a [rare earth] metal selected from the group consisting essentially of *rare earth metals including* yttrium, zirconium[,] *and* niobium[, and molybdenum]. These metals have a filter K-edge energy of [20.0] *20* keV or less. With the above described filter apparatus using these [rare earth] metals as the filter material, the filter is very thin and largely transparent to photons of the energy level of the K-edge energy of the absorption material. By concentrating on the K-edge energy of the filter material, in accordance with the present invention rather than the thickness of the filter material, the photon energy of the radiation beam below 20 keV is eliminated, thus eliminating the portion of the photon energy levels of the radiation beam considered to contribute little to the quality of the radiographic image.

AS A RESULT OF REEXAMINATION, IT HAS BEEN DETERMINED THAT:

Claims 1–3, 7–9 and 11 are determined to be patentable as amended.

Claims 4–6, 10 and 12, dependent on an amended claim, are determined to be patentable.

1. Apparatus for limiting the radiation dosage to an examination object within a limited photon energy range comprising,
   - a source of radiation including an X-ray generator for emitting a beam of penetrating radiation toward the examination object,
   - said X-ray generator having a slot through which said beam of radiation passes,
   - a radiation beam limiting device positioned on said X-ray generator in overlying relation with said slot,
   - a protective filter positioned in the path of said beam between said source and the examination object,
   - said protective filter being supported by said radiation beam limiting device such that the center of the radiation beam emitted from the X-ray generator passes through said protective filter,
   - said protective filter composed of a *metallic* material *selected from a group consisting essentially of rare earth metals, zirconium and nibium* have a preselected critical absorption edge energy operable to obstruct from the beam photonenergy below 20 keV and permit a filtered beam having a photon energy above 20 keV to pass through the examination object,
   - a radiation detector positioned to receive the filtered radiation emerging from the examination object,
   - said radiation detector being operable to generate an output signal corresponding to the intensity of the emerging filtered radiation, and
   - image processing means for converting said output signal to a radiographic image displaying the examination object.

2. Apparatus as set forth in claim 1 in which,
   - said protective filter includes a [rare earth] metallic foil.

3. Apparatus as set forth in claim [2] *1* in which,
   - said rare earth [metallic foil] *metal* is [selected from a group of filter materials consisting essentially of] yttrium[, zirconium, niobium and molybdenum].

7. Apparatus for limiting the radiation dosage to an examination object within a limited photon energy comprising,
   - a source of radiation for emitting a beam of penetrating radiation toward the examination object,
   - a radiation beam limiting device positioned a preselected distance from said radiation source and between said radiation source and the examination object,
   - a protective filter positioned in the path of said beam between said radiation source and the examination object,
   - said protective filter being supported by said radiation beam limiting device such that the center of said radiation beam emitted from said radiation source passes through said protective filter,
   - said protective filter including metallic foil *selected from the group consisting essentially of rare earth metals, zirconium and niobium* having a preselected thickness in the range between about 100 microns to 250 microns and is operable to obstruct from the radiation beam photon energy less than 20 keV and permit photon energy greater than 20 keV to pass through said metallic foil and the examination object,
   - a radiation detector positioned to receive the filtered radiation emerging from the examination object,
   - said radiation detector being operable to generate an output signal corresponding to the intensity of the emerging filtered radiation, and
   - image processing means for converting said output signal to a radiographic image displaying the examination object.

8. Apparatus as set forth in claim 7 in which,
   - said protective filter is a *rare earth* metallic foil [selected from the group of rare earth metals] consisting [essentially] of yttrium[, zirconium, niobium, and molybdenum].

9. A method for limiting the radiation dosage to an examination object comprising the steps of,
   - emitting a beam of penetrating radiation from a source of radiation toward the examination object,
   - positioning a filter material a preselected distance from the source of radiation and the examination object between the source of radiation and the examination object,
   - providing a filter material having a preselected thickness in the range between about 100 microns and 250 microns and selected from the group of [rare earth] metals consisting essentially of *rare earth metals,* yttrium, zirconium [,] *and* niobium [, and molybdenum], obstructing radiation beam photon energy of 20 keV and less by the filter material, permitting photon energy of the radiation beam above 20 keV to pass through the examination object, detecting the filtered radiation emerging from the examination object, and processing the emerging filtered radiation to provide a radiographic image of the examination object corresponding to the intensity of the emerging filtered radiation.

11. A method for limiting the radiation dosage to an examination object comprising the steps of, emitting a radiation beam from an X-ray generator to the examination object, supporting a filter material on the X-ray generator such that the center of the radiation beam passes through the filter, selecting the filter material having a preselected thickness in the range between about 100 microns and 250 microns and from the group of [rare earth] metals consisting essentially of *rare earth metals,* yttrium, zirconium [,] *and* niobium [, and molybdenum], obstructing by the filter material radiation beam photon energy of 20 keV and less and being transparent to photon energy of 20 keV and less and being transparent to photon energy above 20 keV, permitting photon energy of the radiation beam above 20 keV to pass through the examination object, detecting the filtered radiation emerging from the examination object, and processing the emerging filtered radiation to provide a radiographic image of the examination object corresponding to the intensity of the emerging filtered radiation.

* * * * *